United States Patent

Albrechtsen et al.

[11] Patent Number: 5,939,100
[45] Date of Patent: Aug. 17, 1999

[54] COMPOSITION FOR DRUG DELIVERY COMPRISING NICOTINE OR A DERIVATIVE THEREOF AND STARCH MICROSPHERES AND METHOD FOR THE MANUFACTURING THEREOF

[75] Inventors: Sten Albrechtsen, Hilleröd; Lene Orup-Jacobsen, Gentofte; Jens Hansen, Alleröd; Birgitte Möllgaard, Virum, all of Denmark

[73] Assignee: Pharmacia and UpJohn AB, Helsingborg, Sweden

[21] Appl. No.: 08/640,873

[22] PCT Filed: Oct. 3, 1994

[86] PCT No.: PCT/SE94/00917

§ 371 Date: Aug. 26, 1996

§ 102(e) Date: Aug. 26, 1996

[87] PCT Pub. No.: WO95/12399

PCT Pub. Date: May 11, 1995

[30] Foreign Application Priority Data

Nov. 1, 1993 [SE] Sweden .................................. 9303574

[51] Int. Cl.[6] ........................................................ A61K 9/14
[52] U.S. Cl. ............................ 424/489; 424/1.11; 424/470
[58] Field of Search ..................................... 424/1.11, 489, 424/470; 514/214, 343

[56] References Cited

U.S. PATENT DOCUMENTS

| 865,026 | 9/1907 | Ellis . |
| 940,521 | 11/1909 | Endicott . |
| 3,845,217 | 10/1974 | Ferno et al. . |
| 3,877,468 | 4/1975 | Lichtneckert et al. . |
| 3,901,248 | 8/1975 | Lichtneckert et al. . |
| 4,124,705 | 11/1978 | Rothman et al. ...................... 424/1.11 |
| 4,579,858 | 4/1986 | Ferno et al. ............................. 514/343 |
| 4,915,950 | 4/1990 | Miranda et al. . |
| 5,026,697 | 6/1991 | Lotsof ..................................... 514/214 |
| 5,167,242 | 12/1992 | Turner et al. . |
| 5,204,108 | 4/1993 | Illum . |

FOREIGN PATENT DOCUMENTS

| 122036 | 4/1987 | European Pat. Off. . |
| 219276 | 11/1994 | European Pat. Off. . |
| 2313996 | 10/1974 | Germany . |
| 1528391 | 10/1978 | United Kingdom . |
| 2030862 | 4/1980 | United Kingdom . |
| WO 88/09163 | 12/1988 | WIPO . |
| WO 89/03207 | 4/1989 | WIPO . |
| WO 91/09599 | 7/1991 | WIPO . |

OTHER PUBLICATIONS

J. Pharm. Pharmacol., vol. 45, Apr. 1993, B.C. Thanoo et al., "Controlled Release of Oral Drugs from Cross–linked Polyvinyl Alcohol Microspheres".

Primary Examiner—Thurman K. Page
Assistant Examiner—William E. Benston, Jr.
Attorney, Agent, or Firm—Gilberto M. Villacorta; Pepper Hamilton LLP

[57] ABSTRACT

A powdery pharmaceutical composition comprising nicotine or a derivative thereof and starch microspheres. The starch microspheres are preferably degradable epichlorhydrin cross-linked starch microspheres. The average diameter of the microspheres is from around 1 μm to around 200 μm, preferably around 45 μm. The invention also encompasses a method for manufacturing a powdery pharmaceutical composition comprising nicotine and starch microspheres. The invention further comprises a method of diminishing the desire of a subject to use tobacco which comprises the step of administering to the subject the above powdery pharmaceutical composition.

26 Claims, 2 Drawing Sheets

COMPOSITION FOR DRUG DELIVERY COMPRISING NICOTINE OR A DERIVATIVE THEREOF AND STARCH MICROSPHERES AND METHOD FOR THE MANUFACTURING THEREOF

FIELD OF THE INVENTION

The present invention concerns a composition for drug delivery and a method for the manufacturing thereof. Specifically the invention concerns a composition in which a drug is bound to starch microspheres. The composition according to the invention is of particular interest for nasal delivery. The composition is primarily intended as an aid in nicotine replacement therapy.

OBJECTIVES OF THE INVENTION

A primary objective of the invention is to provide for a new and inventive pharmaceutical composition for nasal, oral, buccal or pulmonary administration of nicotine. The objective is achieved with a powdery composition comprising nicotine incorporated in degradable starch microspheres.

A further objective of the invention is to provide for a method of incorporating nicotine into starch microspheres.

A still further objective of the invention is to provide for a method for diminishing the desire of a person to use tobacco which comprises administering to that person a composition comprising nicotine incorporated into degradable starch microspheres.

BACKGROUND

Figure 1:
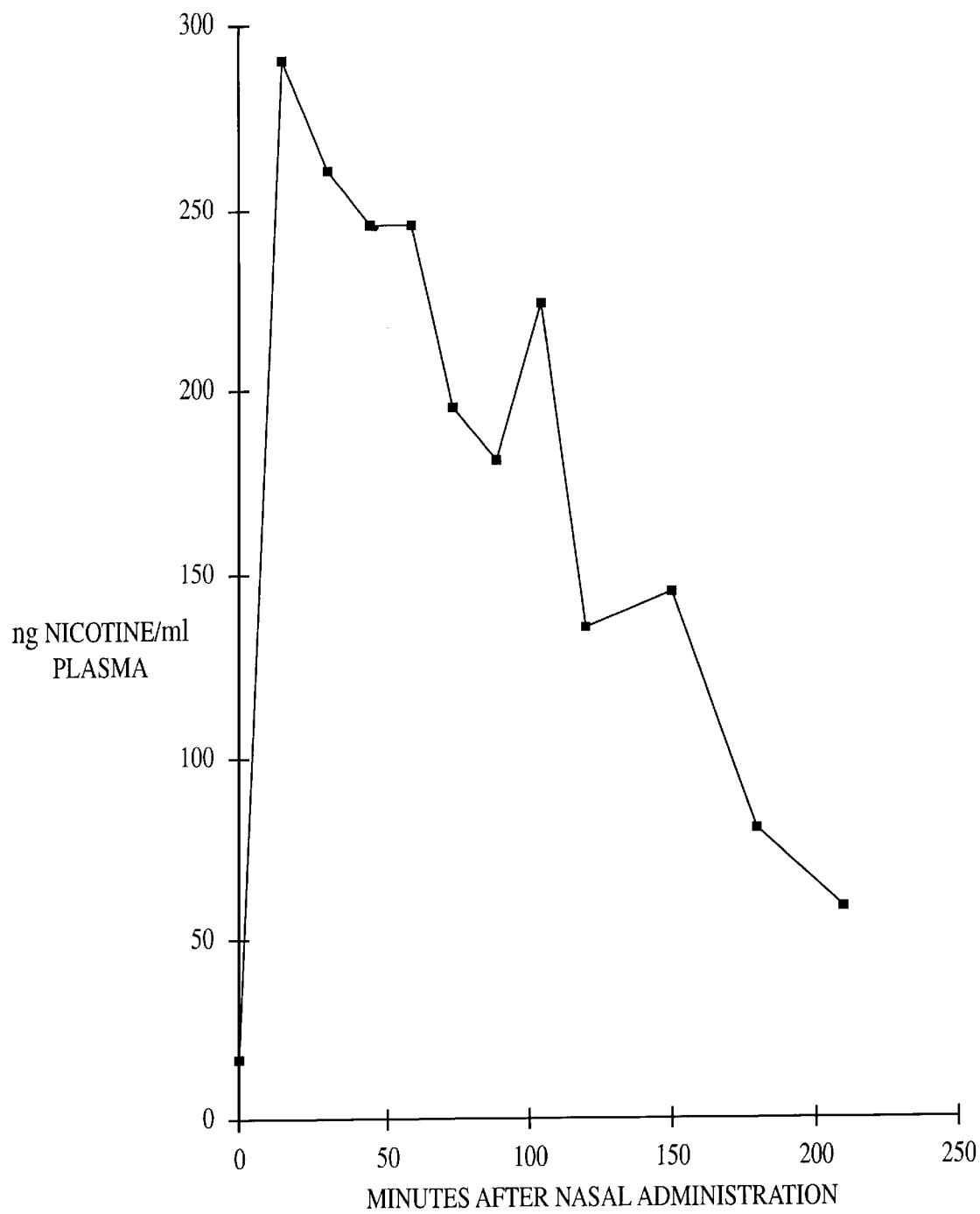
FIG. 1 illustrates the mean nicotine concentration in the plasma of rats as a function of time after nasal absorption of nicotine from the nicotine-Spherex® microspheres.

In the U.S. Surgeon General's 1979 report on Smoking and Health, it was estimated that in the U.S. alone about 350,000 deaths are caused each year by diseases related to cigarette smoking. In fact, excessive smoking is now recognized as one of the major health problems throughout the world.

The most advantageous thing a heavy smoker can do is, therefore, to reduce or preferably even stop smoking completely. Experience shows, however, that most smokers find this extremely difficult. It is generally accepted that this difficulty results from the fact that heavy smokers are dependent on nicotine, which is considered to be one of the risk factors in tobacco smoke. The most important risk factors, however, are substances which are formed during the combustion of tobacco, such as carbon monoxide, tar products, aldehydes, and hydrocyanic acid.

One way to reduce smoking would, of course, be to provide nicotine in a form or manner other than by smoking. There are available tobacco products which can be used for this purpose, such as chewing tobacco and snuff, which latter material can be administered both via nasal and oral routes. Tobacco products of this type are, however, not without harmful effects, such as cancer, and are not well accepted socially. One already existing product, which fulfils the above-mentioned objective of providing nicotine in a less harmful and more socially-acceptable manner, is a nicotine chewing gum. Nicotine-containing chewing gums are not new. U.S. Pat. Nos. 865,026 and 940,521 are representative of ancient efforts along these lines. More recently, however, U.S. Pat. Nos. 3,877,468, 3,901,248 and 3,845,217 have appeared, and the products of the latter of these three patents are now being marketed on an international scale. These products combine a nicotine-containing cation exchange resin complex in gum base, preferably together with a buffering agent which maintains the pH of the saliva above its normal physiological pH.

It seems particularly difficult to find other smoking substitutes equivalent to or as effective as the chewing gum substitutes just mentioned, and the aerosol compositions of the Gildermeister or Smith British Pat. Nos. 1,528,391 or 2,030,862, adapted to be sprayed into the mouth of the user, are hardly an answer to the problem and in actuality appear to be merely a particular extension of a suggestion made as early as 1967 (A. Herxheimer et al, Lancet 1967, II 754–5).

Unilever in German Offenlegungsschrift No 2,313,996, published Oct. 10, 1974, describes certain water-soluble readily-absorbed snuff powders and a process for their manufacture, but these involve only extracts of tobacco aroma combined with solid water-soluble adsorbents. Such snuff substitutes are supposedly less prone to discolour teeth, fingers, and so on, but contribute nothing as far as the problem presently under consideration and certainly suggest no socially-acceptable solution with respect thereto.

In recent years transdermal administration of nicotine by way of patches has been suggested, i.a. by Miranda et al in U.S. Pat. No. 4,915,950.

Ingestion of nicotine vapors orally has been disclosed by Turner et al in U.S. Pat. No. 5,167,242. The authors suggest a nicotine-impermeable container and a nicotine inhaling device in which the container is placed. The inhaling device has outer resemblancies with a cigarette and is supposed to be "smoked" like a cigarette although no pyrolysis takes place.

One socially- and toxicologically-acceptable way of administering nicotine is by way of the administration directly into the nasal cavity. A smoking substitute for application directly into the nose was disclosed by Fernö, Helgertz and Ohisson in U.S. Pat. No. 4,579,858. This substitute is in the form of an aqueous nicotine solution characterized by defined ranges for nicotine concentration, pH value and viscosity.

Although said aqueous solution provides for a useful way of nasal administration of nicotine it has certain drawbacks, such as irritative effects on the nasal mucosa. Even if the bioavailability of the above aqueous nicotine is fairly high it would be of advantage if the bioavailability for nasally administered nicotine could be increased thereby decreasing the amount of nicotine needed to be administered for arriving at a certain plasma concentration.

Minute polysaccharide particles which may be used in the present invention were disclosed by Rothmann and Lindberg in U.S. Pat. No. 4,124,705. The particles according to this patent are intended for intravascular administration in a suspension. Upon administration said particles block the finer blood vessels of the body. The authors disclose coadministration of the polysaccharide particles and a diagnostic agent. Anyhow Rothmann and Lindberg do neither suggest nasal administration nor the incorporation of nicotine into the particles.

Administration of drugs to the nasal mucosa can be done by way of powdery pharmaceutical compositions for application to the nasal mucosa. Lisbeth Ilium discloses in WO 88/09163 a drug delivery system including a plurality of microsphere particles containing an active drug and including a surfactant material associated with each particle. The particles may be made of i.a. starch or gelatin. Suitable drugs include vaccine and polypeptides. Lisbeth Illum discloses in WO89/03207 a drug delivery composition, for i.a. nasal administration, comprising a plurality of microspheres and active drug associated with each such microsphere. The drugs have a maximum molecular weight of 6.000 and the microspheres may be of starch, gelatin or albumin. Suitable drugs include insulin and antigenic vaccine ingredients. Nicotine is not suggested neither in WO 88/09163 nor in WO89/03207.

TEIJIN LIMITED discloses in EP 122 036 a powdery pharmaceutical composition for nasal administration comprising a water-absorbing and water-insoluble base. This base might be i.a. starch. This invention is anyhow limited to the administration of a physiologically active polypeptide. There is no mentioning of nicotine in EP 122 036.

EXAMPLES

The invention will be illustrated by a few non-limiting examples.

Materials

Nicotine base was purchased from Kodak (batch No 42904).

Degradable Starch Microspheres (DSM) particles were obtained from Kabi Pharmacia, Sweden. Their registration trademark is Spherex®.

Degradable Starch Microspheres (DSM) used in the present invention are characterized in the above mentioned patent U.S. Pat. No. 4,124,705 in which also are disclosed methods for their manufacturing. The DSM substance consists of a polymeric matrix of cross-linked starch of complex chemical structure and, therefore, cannot be described simply by means of a conventional chemical name. The INN name is amilomer, amilomerum. The substance cannot, for the same reason as above, be meaningsfully represented by a single structural formula. The chemical structure of starch microspheres is composed of starch fragments from hydrolyzed potato starch crosslinked and substituted with glycerol ether moieties. These occur as single as well as oligomeric crosslinks of substituents with varying substructure.

The molecular weight of the polymeric network of the matrix is undefined and may be assumed to be infinite. The size of the starch microspheres is characterized by a diameter distribution measured as volume distribution on swelled beads. The average diameter is 45 $\mu$m and more than 95% of the microspheres have a diameter between 20 and 70 $\mu$m.

In short the Spherex® particles used in the present invention can be characterized as degradable epichlorhydrin cross-linked starch microspheres with a mean diameter of 45 $\mu$m when swollen and a biological degradation time (t½) of 25 minutes when degraded in 240 IU/ml amylase solution.

The Spherex® particles used in the present invention have several functions: The particles acts as a drug carrier. When deposited in the nasal cavity, the clearance due to mucusal flow is reduced. By taking up water it is believed that the particles dehydrate the nasal epithelium thereby opening the tight junctions connecting the cells and thus increasing the paracellular uptake of the drug.

Example 1

Preparation of Lyophilised Formulations

The nicotine-Spherex® batch used for the biological experiments according to the following Example 2 was prepared by mixing 100 mg Spherex® particles with 850 $\mu$l 2% nicotine solution in demineralised water corresponding to 17 mg nicotine base/100 mg Spherex® particles. This mixture equilibrated for 1 hour at room temperature and was thereafter freeze dried to obtain a powdery formulation. The freeze dried material was sieved through a 60 $\mu$m sieve before use.

Example 2

Estimation of the Bioavailability of Nicotine Bound to Spherex®Microspheres When Administered Intranasally

Rat Studies

Male Lewis rats (Lew/Mol) purchased from Mollegaard, Denmark, were used for the studies. The animals were fed unlimited on Altromin 1324 and supplied with tap water. The rats were fasted 18–24 hours prior to experimental start. The rats weighed not less than 200 g when used for experiments.

The rats were anaesthetized with Mebumal (50 mg/ml) in an initial dose of 50 mg/kg bodyweight (i.p.). If signs of reflexes were observed during the experiment, a supplementary dose (10 mg/kg) was given.

The anaesthetized rats were fixated on thermostated plates maintaining a body temperature of 37° C. The trachea was cannulated using a PE 200 polyethylene tubing thus assessing free airways. The anterior part of the trachea was dosed with surgical thread thus leaving nasal formulations/administrations in the anterior part of the airways. The oesophagus was dosed for the same reasons.

The aorta carotis was cannulated using a 24 G/¾" indwelling cannula. Vena femoralis was similarly cannulated to secure a constant blood volume due to blood sampling. Blood samples (250 $\mu$l) were withdrawn from aorta carotis and an equal volume physiological saline was injected through vena femoralis.

Lyophilized nicotine-Spherex® microspheres prepared in accordance with Example 1 were administered by blowing the powder into one of the nostrils of the rat. The powdery formulation was deposited in a PE 90 polyethylene tubing in an amount corresponding to a dose of approx. 7 mg powdery formulation/kg SW. When administering the powder, the tubing was guided into the nostril and the content blown out by blowing 500 $\mu$l air through the tubing by use of a syringe.

The amount of powder administered was calculated by weighing the tubing before and after administration.

For the calculation of the bioavailability of the nicotine when administered intranasally, intravenous injections of nicotine were performed. The experimental setup was the same as described above, except for the administration of nicotine which was injected into vena femoralis (0.15 mg nicotine/kg BW from a solution of 0.3 mg nicotinelml physiological saline).

Calculation of Pharmacokinetic Parameters

The pharmacokinetic parameters were determined using the SIPHAR/Kinetics software program from SIMED (France).

Intranasal Administration

The plasma values from each animal were plotted in a semi-logaritmic plot whereby the number of phases could be determined visually. Two phases were observed.

The data were therefore analysed assuming one compartment of distribution and two phases, an absorption and an elimination phase.

The model was fitted to the data using weighed least squares algoritm with the weighing factor=1.

Intravenous Administration

The plasma values obtained after i.v. administration of nicotine were just like those obtained by intranasal administration analysed for the number of phases.

One phase was recognized corresponding to only one elimination phase.

The model was fitted to the data using weighted least squares algoritm with the weighing factor=1.

The bioavailability was calculated as follows:

$$\text{Bioavailability}(\%) = \frac{(AUC_{i.n.}/\text{Dose})}{(AUC_{i.v.}/\text{Dose})} \times 100$$

AUC (Area Under the Curve) was calculated by the SIPHAR program using the trapezoidal rule.

Determination of Nicotine in Rat Plasma

Blood Samples

Blood samples (100 pi) were placed in centrifuge tubes added Heparin (3.4 μl, 3 U/ml). The tubes were centrifuged at 823 g for 15 min. The plasma supematants were transferred to new tubes and kept at −22° C. until analysis.

Principle

After precipitation of plasma proteins, nicotine in the organic supematant was determined by capillary gas chromatography using a nitrogen phosporus detector.

Determination of Nicotine in the Spherex® Microspheres

The theoretical concentration of nicotine in the freeze-dried nicotine-Spherex® formulation was 17 mg/100 mg Spherex® microspheres. The actual concentration was determined by HPLC-analysis after 1 hour's extraction/degradation of the product in 0.025 M HCI. The actual content was by this method determined to be 14.2 mg nicotine base/100 mg Spherex® particles.

Intranasal Administration of Nicotine-Spherex®-Microspheres

The nasal absorption of nicotine from the nicotine-Spherex® microspheres was investigated in 10 rats. The mean nicotine concentrations in plasma as a function of time are shown in the below Table 1 and FIG. 1.

TABLE 1

Plasma nicotine values after intranasal administration of Spherex ® nicotine microspheres. The mean dose was 6.46 ± 0.58 mg Spherex/kg BW.

| Minutes after nasal adm. | Average for 10 rats | St. Dev |
|---|---|---|
| 0 | 17 | 47,2 |
| 15 | 291 | 138,5 |

TABLE 1-continued

Plasma nicotine values after intranasal administration of Spherex ® nicotine microspheres. The mean dose was 6.46 ± 0.58 mg Spherex/kg BW.

| Minutes after nasal adm. | Average for 10 rats | St. Dev |
|---|---|---|
| 30 | 260 | 77,3 |
| 45 | 245 | 104,8 |
| 60 | 245 | 109,5 |
| 75 | 194 | 91,8 |
| 90 | 180 | 116,5 |
| 105 | 223 | 116,4 |
| 120 | 134 | 34,4 |
| 150 | 144 | 72,5 |
| 180 | 78 | 71,9 |
| 210 | 56 | |

The data from all 10 experiments were used to calculate one set of pharmacokinetic parameters. This procedure was legal since the variation in drug dose was small (6.4±0.58 mg Spherex® particles/kg BW) and so was the variation in body weight (242 g±22 g).

The intranasal administration of nicotine-Spherex® microspheres resulted in a plasma peak value of 291 ng nicotine/ml plasma, which was obtained within 15 minutes after administration (t½=1.89 min).

The pharmacokinetic parameters calculated by the SIPHAR-program are tabulated in the below Table 2 together with their standard deviation (SD). The elimination coefficient, $K_e$, is fairly accurately determined but the absorption coefficient, $K_a$, has a very large SD, probably due to too few data points representing the uptake phase.

TABLE 2

| Parameter | Parameter value | S.D. | C.V. (%) | Half-life (minutes) |
|---|---|---|---|---|
| $K_e$ | 0.3662 | 2.1858 | 596.9 | 1.89 |
| $K_a$ | 0.0056 | 0.0016 | 29.6 | 125 |

The $AUC_{0-\infty}$ was calculated to a value of 56226 ng/ml× min.

Intravenous Administration of Nicotine

Figure 2:
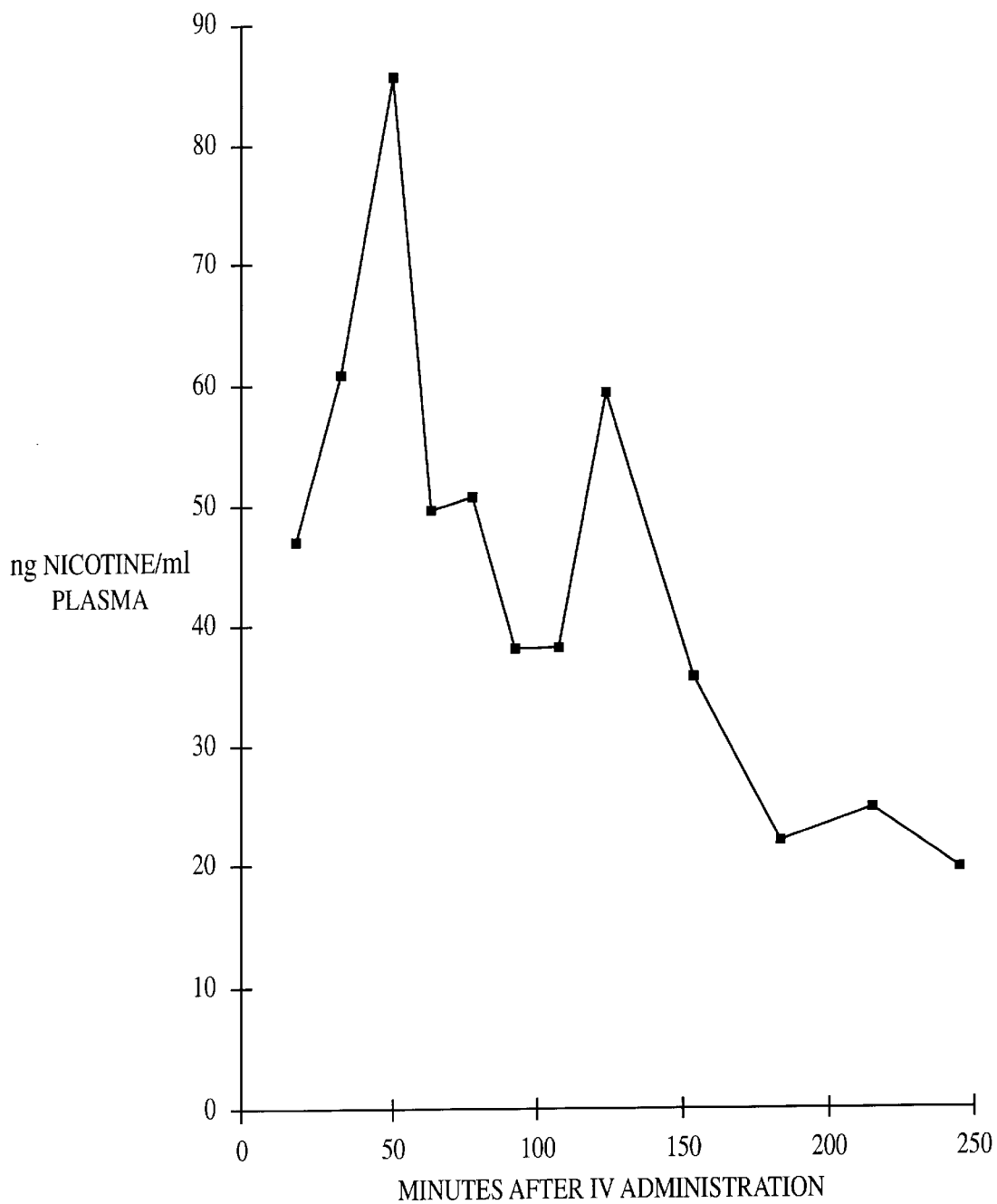
FIG. 2 shows the plasma nicotine values as a function of time in animals after i.v. administration of nicotine.

The plasma nicotine values as a function of time after i.v. administration of nicotine are shown in the below Table 3 and FIG. 2. Six animals were used in the study. The pharmacokinetic parameters are calculated as described for the data obtained by intranasal administration.

TABLE 3

Plasma nicotine values after intravenous administration of nicotine. The nicotine dose was 0.15 mg/kg BW.

| Minutes after I.v. adm., | Average for 6 rats | St. Dev. |
|---|---|---|
| 15 | 47 | 36,1 |
| 30 | 61 | 23,9 |
| 45 | 86 | 78,1 |
| 60 | 50 | 43,1 |
| 75 | 51 | 32,2 |
| 90 | 38 | 50,0 |
| 105 | 38 | 38,3 |

TABLE 3-continued

Plasma nicotine values after intravenous administration of nicotine. The nicotine dose was 0.15 mg/kg BW.

| Minutes after I.v. adm., | Average for 6 rats | St. Dev. |
|---|---|---|
| 120 | 59 | 55,4 |
| 150 | 36 | 36,0 |
| 180 | 22 | 52,0 |
| 210 | 25 | 19,1 |
| 240 | 20 | 33,5 |

The elimination coefficient, $K_g$, is shown in the below Table 4.

TABLE 4

| Parameter | Parameter value | S.D. | C.V. (%) | Half-life (minutes) |
|---|---|---|---|---|
| $K_e$ | 0.0044 | 0.0022 | 49.93 | 156 |

An $AUC_{0-\infty}$ has been calculated. The value was 15717 ng/ml×min.

Bioavailability

The bioavailability was calculated as:

$$\text{Bioavailability}(\%) = \frac{(AUC_{i.n.}/\text{Dose})}{(AUC_{i.v.}/\text{Dose})} \times 100$$

The bioavailability was calculated to 58% for the intranasal formulation.

Further Embodiments

The powdery pharmaceutical composition according to the present invention might be administered not only via the nasal route, but possibly after modification within the scope of the invention, also orally, pulmonary or buccally.

Different additives, such as buffers, absorption enhancers, flavors and stabilizing agents, may be incorporated into the microspheres together with the nicotine in essentially the same way as the nicotine was incorporated according to the above Example 1.

In the above Examples 1 and 2 was used nicotine in the form of nicotine base. Using essentially the same method as in Example 1 nicotine might instead be incorporated in the form of a salt or a molecular complex or combinations thereof including or not including also nicotine as a free base.

In the above Examples 1 and 2 were used starch microspheres with an average diameter of 45 µm. Anyhow smaller as well as bigger particles might also be used without significant change in the bioavailability of the incorporated nicotine. A useful diameter range is from about 1 µm to about 200 µm. Particles within this diameter range are essentially deposited in the nasal cavity when administered nasally without being further transported to the lungs. Such particles are also to a great extent transported to the lungs when administered perorally.

The particles used in the above Examples 1 and 2 contain about 14 mg nicotine base/100 mg starch microspheres. This concentration should anyhow not be regarded as the only possible or optimal concentration. Using different forms of nicotine it is possible to arrive at a very high concentration of nicotine in microspheres, up to 100 mg nicotine/100 mg unloaded starch microspheres, without thereby destroying the microspheres. The preferred concentration range, 12–40 mg nicotine/100 mg unloaded starch microspheres, is fairly wide due to the fact that when using microspheres with a high nicotine content a comparably small amount of microspheres is administered in order to arrive at the desired plasma concentration and vice versa.

We claim:

1. A pharmaceutical composition comprising nicotine or a derivative thereof and starch microspheres, wherein said composition is adapted to be administered to a subject in need thereof by at least one method consisting essentially of nasally, orally, pulmonarily, and buccally.

2. The composition of claim 1 in which the starch microspheres are degradable.

3. The composition of claim 1 in which the microspheres have a diameter between 0.1 and 200 µm.

4. The composition of claim 3 in which the average microsphere diameter is around 45 µm when swollen.

5. The composition of claim 1 in which the nicotine is in the form of a free base, a salts a molecular complex, or combinations thereof.

6. The composition of claim 1 which further comprises one or more additives.

7. The composition of claim 1 which is adapted for nasal administration.

8. The composition of claim 1 which is adapted for oral administration.

9. The composition of claim 1 which is adapted for pulmonary administration.

10. The composition of claim 1 which is adapted for buccal administration.

11. The composition of claim 1 in which the nicotine concentration is from around 1 mg nicotine/100 mg unloaded starch microspheres to around 100 mg nicotine/100 mg unloaded starch microspheres.

12. A process for making a pharmaceutical composition comprising nicotine or a nicotine derivative, wherein said process comprises:

(a) mixing starch microspheres with an aqueous solution comprising at least one of nicotine or a derivative of nicotine to form a mixture, wherein said starch microspheres are from about 1 to about 200 micrometers in diameter, and wherein said at least one of nicotine or a derivative of nicotine is present in the mixture at a concentration of from about 2 to about 100 milligrams per 100 milligrams of said starch microspheres;

(b) allowing the mixture to equilibrate for a period of time from about 0.1 to about 24 hours, and (c) drying the equilibrated mixture to obtain a powdery formulation.

13. The process of claim 12 in which the starch microspheres are degradable.

14. A method of diminishing the desire of a subject to smoke or sniff tobacco or chew tobacco comprising administering to the subject a powdery pharmaceutical composition of claim 1.

15. The composition of claim 2 in which the starch microspheres are comprised of epichlorhydrin cross-linked starch microspheres.

16. The composition of claim 4 in which more than 95% of the microspheres have a diameter between 20 and 70 µm when swollen.

17. The composition of claim 6 in which the one or more additives is selected from the group consisting of buffers, absorption enhancers, flavors, or stabilizing agents.

18. The composition of claim 11 in which the nicotine concentration is from around 12 mg nicotine/100 mg unloaded starch microspheres to around 40 mg nicotine/100 mg unloaded starch microspheres.

19. The process of claim 12 which further comprises sieving the mixture of step (c).

20. The process of claim 12 in which the mixture of step (b) is freeze-dried in step (c).

21. A method as claimed in claim 14 comprising administering said pharmaceutical composition to said subject by at least one method consisting essentially of nasal administration, oral administration, pulmonary administration and buccal administration.

22. A method as claimed in claim 21 wherein said pharmaceutical composition is administered nasally.

23. A method as claimed in claim 21 wherein said pharmaceutical composition is administered orally.

24. A method as claimed in claim 21 wherein said pharmaceutical composition is administered pulmonarily.

25. A method as claimed in claim 21 wherein said pharmaceutical composition is administered buccally.

26. The method of claim 12 in which said concentration of at least one of nicotine or a derivative of nicotine in said mixture is from about 12 to about 40 milligrams per 100 milligrams of said starch microspheres.

* * * * *